United States Patent [19]

Beoni

[11] Patent Number: 5,180,391
[45] Date of Patent: Jan. 19, 1993

[54] MIDDLE EAR PROSTHESIS

[76] Inventor: Franco Beoni, Via Venturini 6, 29100 Piacenza, Italy

[21] Appl. No.: 568,217

[22] Filed: Aug. 16, 1990

[30] Foreign Application Priority Data

Jun. 7, 1990 [IT] Italy .................. 20570 A/90

[51] Int. Cl.⁵ .................................. A61F 2/18
[52] U.S. Cl. ........................................ 623/10
[58] Field of Search ............................ 623/10

[56] References Cited

U.S. PATENT DOCUMENTS

| | | | |
|---|---|---|---|
| 3,473,170 | 10/1969 | Haase et al. | 623/10 |
| 3,838,468 | 10/1974 | Armstrong | 623/10 |
| 4,169,292 | 10/1979 | Grote | 623/10 |
| 4,281,419 | 8/1981 | Treace | 623/10 |
| 4,601,723 | 7/1986 | McGrew | 623/10 |
| 4,740,209 | 4/1988 | Gersdorff | 623/10 |
| 4,817,607 | 4/1989 | Tatge | 623/10 |
| 4,957,507 | 9/1990 | Lenkauskas | 623/10 |

Primary Examiner—David Isabella
Attorney, Agent, or Firm—Ladas & Parry

[57] ABSTRACT

A middle ear prosthesis comprises a circular ring of substantially rigid synthetic material of a type able to bond to the osseous tissue if placed in contact with it; an elastic membrane of synthetic material compatible with the human body and fixable to the ring to close it; a columellar element of material compatible with the human body comprising a rigid but curvable intermediate portion; first connection means for connecting the intermediate portion to the central region of the membrane; and second connection means for fixing the intermediate portion to the stapes or to that part of it which remains.

20 Claims, 2 Drawing Sheets

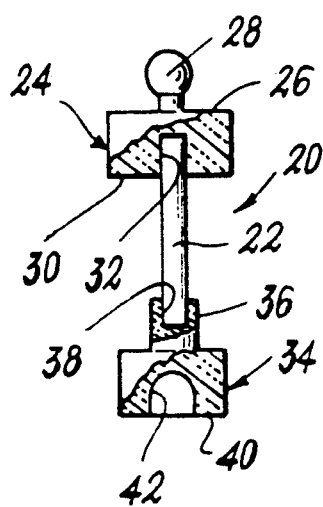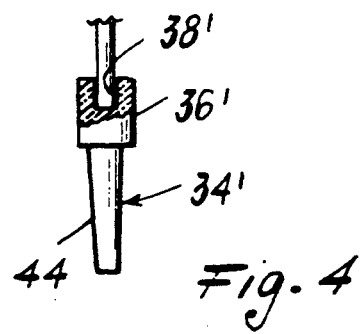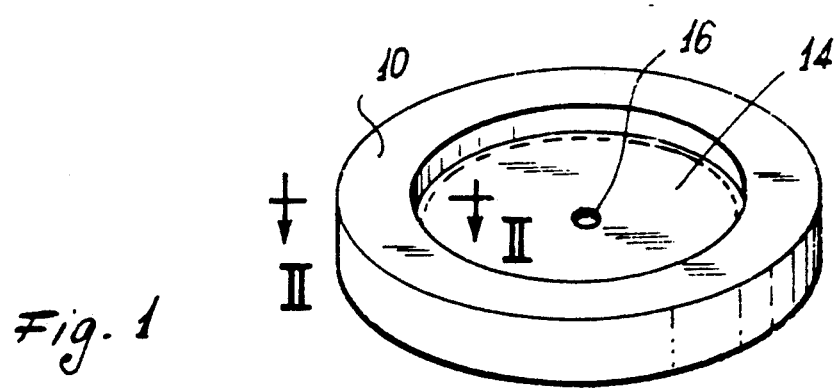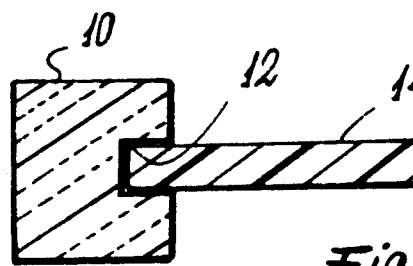

MIDDLE EAR PROSTHESIS

BACKGROUND OF THE INVENTION

1. Field of the Invention

This invention relates to a middle ear prosthesis.

2. Description of Prior Art

The purpose of tympanoplasty is to reconstruct the eardrum and ossicles (stapes, incus and malleus) of the middle ear which have been destroyed by otitis.

Hitherto this type of surgery has been carried out by the following methods:

1) to reconstruct the eardrum a piece of the temporalis or other tissue of the same patient or alternatively animal tissue deproteinized to prevent rejection are used; to reconstruct the ossicle chain, ceramic or plastic prostheses or remodelled tissue of the patient are used;

2) in the case of homotransplant, an eardrum-ossicle block taken from a cadaver is repositioned in the ear to be reconstructed.

These various reconstructions have the serious drawback of being subject to displacement, reabsorption or rejection, resulting in operational failure. In this respect the surgeon must himself during the surgery construct the parts required for the reconstruction, or in the most favourable case combine partial prostheses (such as ceramic or plastic ossicles) with parts constructed on the spot. Because of this situation the result of the surgery is often dependent on the manual dexterity of the surgeon, which is very variable.

From the foregoing it is apparent that no satisfactory method has as yet been found by which the aforesaid problems which occur with the passage of time are avoided. In the present state of the art about 50% of tympanoplasty operations fail within five years.

SUMMARY OF THE INVENTION

The object of the present invention is to obviate the aforesaid drawbacks by providing an artificial middle ear prosthesis which takes root without being subject to displacement or reabsorption, is able to function as soon as it is applied or after only a short time period, and gives uniform results in all operated cases.

This object is attained by the middle ear prosthesis according to the invention, characterised by comprising:

a circular ring of substantially rigid synthetic material compatible with the human body and of a type able to bond to the osseous tissue if placed in contact with it;

an elastic membrane of synthetic material compatible with the human body and fixable to said ring to close it;

a columellar element of material compatible with the human body and comprising an intermediate portion of substantially rigid but curvable material;

first connection means for mechanically connecting one end of the intermediate portion of the columellar element to the central region of said elastic membrane; and second connection means for fixing the other end of said intermediate portion to the stapes or to that part of said stapes which remains, said second means consisting of a piece of substantially rigid synthetic material of a type able to bond to the osseous tissue with which it comes into contact.

From tests carried out, it has been found that the artificial middle ear prosthesis of the invention can replace with excellent results the middle ear of a patient which is no longer able to perform its function. In addition, the prosthesis does not suffer from the aforesaid drawbacks of the known art. In one embodiment of the present invention, the first connection means between the intermediate portion of the columellar element and the central region of the elastic membrane consist of a spherical head either integral with the intermediate portion or forming part of an independent piece which can be fixed to the end of the intermediate portion. A hole is provided in the central region of said elastic membrane, the spherical head being insertable through said hole.

In a preferred embodiment of the present invention, if the spherical head forms part of an independent piece this latter consists of the same material as that which forms the circular ring and said first connection piece.

In particular, a piece of wire of a metal compatible with the human body can be used to form the intermediate portion of the columellar element. If the spherical head is in the form of an independent piece this piece conveniently also comprises a cylindrical cavity into which the end of the piece of metal wire can be inserted by slight forcing.

The elastic membrane can be fixed into the circular ring by gluing. Preferably, said circular ring comprises in its inner surface an annular cavity able to receive the edge of said elastic membrane, this edge being inserted by pressure and/or glued into said cavity. The middle ear prosthesis of the present invention has the following advantages:

it has an extremely simple and reliable structure;

all the components of the prosthesis can be constructed in the workshop in the technically most convenient and correct manner to ensure a consistently high product quality;

a complete prosthesis can be supplied to the surgeon ready for fitting, available in a series of models with different dimensional characteristics, to enable the surgeon to choose the most suitable model for the specific case;

the columellar element can be applied and its position checked via the acoustic meatus;

the columellar element can be kept in position by placing pieces of reabsorbable fibrin sponge around it, and then the circular ring with its elastic membrane (replacing the eardrum) be positioned on it and the columellar element be fixed in the centre of the membrane, so that the prosthesis remains accurately fixed in the required position and can no longer move from said position. Such movement occurs however very frequently with known reconstruction methods and is a reason for operational failure. Further advantages will be apparent hereinafter.

At the present time the most convenient material for the membrane is medical grade silicon produced by Dow Corning (USA) and approved for surgical use by the Food and Drug Administration (FDA) because of its bioinert properties. If the membrane is to be glued to the ring, it is convenient to use adhesive based on medical grade silicon.

There is obviously nothing to prevent the circular ring and the columellar element being made to measure for the individual patient. However a significant advantage of the present invention is that the ring can be produced in a series of different diameters to cover all possible requirements. With regard to the columellar element and specifically its intermediate portion, a series of metal wire pieces of various lengths can be provided to again cover all dimensional requirements, whereas the first connection piece and the second connection piece for the columellar element can always have the same dimensions.

The intermediate portion of metal wire, preferably platinum, can be suitable curved at the moment of application to give it the curvature required for the specific case.

In the current state of the art a material which has proved particularly suitable for both the circular ring and the second connection piece for the columellar element is a ceramic material known as hydroxylapatite. The columellar element is produced in two different versions depending on whether the entire stapes is in good condition or if only the footplate of the stapes remains. In the first version the connection piece which forms said second connection means comprises a cavity which marries with the capitellum of the stapes.

In the second version this connection piece has an end which makes contact with the footplate alone (the only part of the stapes which remains).

The method of fitting the prosthesis according to the invention will now be briefly described. The external acoustic meatus is first made regular by cutting, to form in the anulus tympanicus region an annular step to receive the circular ring. This is done by using a milling cutter with a disc of suitable thickness and diameter. A circular ring having a diameter just less than the cut hole and to which the relative elastic membrane is already applied is chosen from the series of available rings and is inserted into the acoustic meatus so that it rests on the step. The cutter used is preferably slightly conical. In this case the circular ring will have the same external taper as the cutter, so that its lateral surface marries with the corresponding surface of the cut hole when the ring is rested on said step. In any event, it is possible to externally adjust the ring by removing material at certain points or by filling any empty spaces between the ring and bone with the constituent material of the ring in powdered form. When the prosthesis has been fitted the sound wave is transmitted by an elastic-mechanical system having much better sensivity and vibratory characteristics than any reconstruction carried out hitherto.

The prosthesis is also easy to fit and has proved to be of long life. It also has a predictable auditory response which is uniform in the various patients operated, and is constant with time. Moreover, it does not suffer from failure due to displacement, necrosis, rejection or the individual rooting-in characteristics of the patient.

Because of its particular structure and the manner in which it is fitted, the described middle ear prosthesis can be removed and refitted by a simple operation. This also enables the tympanic cavity to be checked, and any tumoral formations to be removed if necessary, this having been impossible up to the present time without repeating the entire tympanoplasty.

BRIEF DESCRIPTION OF THE DRAWINGS

The invention will be more apparent from the description of two embodiments thereof given hereinafter by way of example only. In the description, reference is made to the accompanying drawings in which:

FIG. 1 is a perspective view of the circular ring with the elastic membrane already applied;

FIG. 2 is a partial cross-section of the ring of FIG. 1 to an enlarged scale, taken on the line II—II in FIG. 1;

FIG. 3 is a partly sectional side view of a columellar element of the type suitable for connection to a whole stapes;

FIG. 4 is a partly sectional side view of a columellar element of the type suitable for connection to just the footplate of the stapes when the rest of the stapes is unusable.

DESCRIPTION OF THE PREFERRED EMBODIMENTS

Figure 5:
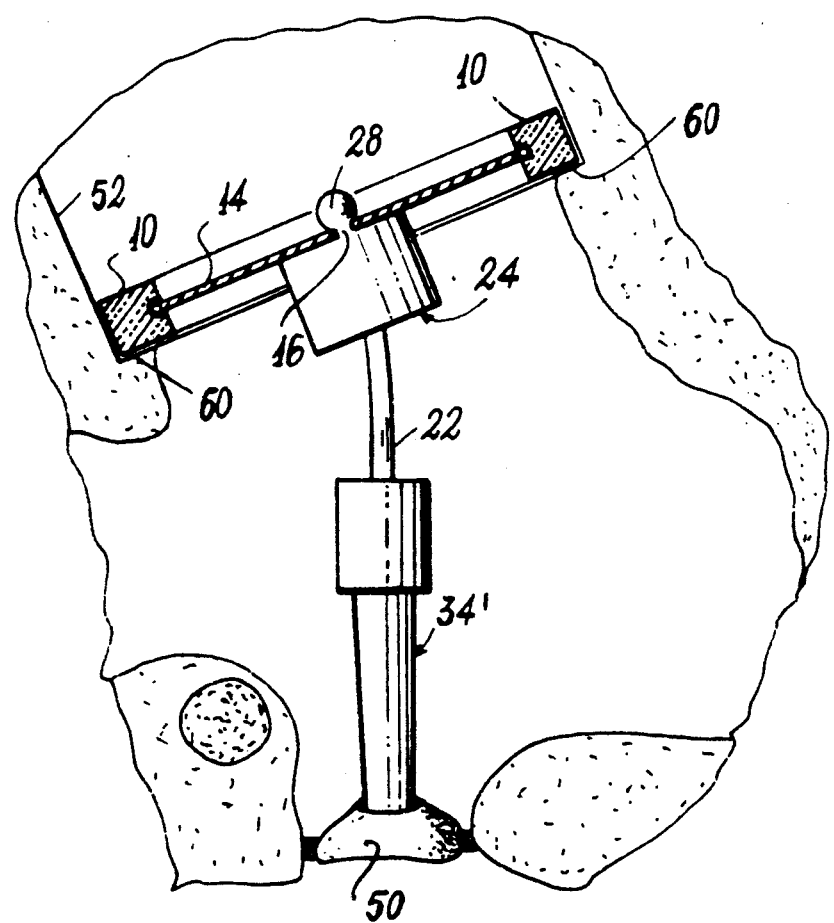
FIG. 5 shows the complete prosthesis applied to the middle ear of the patient, the columellar element being of the type shown in FIG. 4.

As can be seen from FIGS. 1 and 2, the middle ear prosthesis comprises a circular ring 10 of hydroxylapatite. The cross-section through said ring is overall rectangular, with sides differing little in length or equal. The ring 10 comprises an annular groove 12 in its inner side. The edge of a circular elastic membrane 14 of medical grade silicone is inserted into this groove by pressing and/or is glued in position. The membrane has a central hole 16 (FIG. 1) formed by punching during the formation of the membrane from a sheet of silicone of said type.

FIG. 3 shows a columellar element 20 to be connected to the ring 10 complete with its membrane 14. Specifically, the columellar element 20 is of the type having an end shaped to connect to the capitellum of the stapes, if the whole stapes is still completely usable.

The columellar element comprises an intermediate portion 22 formed of wire of a suitable metal compatible with the human body, such as platinum or stainless steel. The metal wire 22 must be able to be curved without breaking, so that it can be adapted to the requirements of the specific patient. An example of this curving is visible in FIG. 5. At one end (the upper end) of the intermediate portion 22 there is provided a first connection piece 24 to allow the intermediate portion 22 to be connected to the elastic membrane 14. From the upper face 26 of the first connection piece 24 there upwardly projects a spherical head 28. This is able to be forced through the circular hole 16 in the membrane 14 so as to securely connect the central part of this latter to the columellar element 20. The first connection piece 24 comprises in its lower face 30 a blind hole 32 into which the relative end of the intermediate portion 22 can be inserted.

At the other (lower) end of the intermediate portion 22 there is a second connection piece 34 provided with an upper boss 36 with a cylindrical cavity 38 into which the relative end of the intermediate portion 22 is inserted. In its lower face 40 the second connection piece 34 comprises a cavity 42 of suitable shape to receive the capitellum of the stapes (not shown).

The metal intermediate portion 22 can be fixed to the first (24) and second (34) connection piece by lightly forcing the relative ends of the metal wire portion 22 into the respective seats 32 and 38.

By heating the columellar element 20 to a temperature close to the melting point of the constituent metal of the intermediate portion 22, a secure connection is obtained between this latter and the first (24) and second (34) connection piece.

If only the footplate of the stapes is usable, with the rest of the stapes no longer being present, the second connection piece 34' has the shape shown in FIG. 4. In this figure it can be seen that a straight tapered rod 44 of hydroxylapatite extends downwards from the boss 38' comprising the cylindrical cavity 36'. FIG. 5 shows a middle ear prosthesis according to the invention already in position. In it the second connection piece (34') is of the type for connection to the footplate 50 of the stapes (the rest of the stapes being absent).

To fit the middle ear prosthesis of the invention, a milled cut is firstly made to regularize the acoustic meatus and form a circular step 60 visible in FIG. 5. The milling cutter should have a thickness at least equal to the thickness of the ring 10 and also a certain degree of taper. In this case, the circular ring 10 to be inserted into the hole 52 obtained in this manner, will have the same external taper as the cutter (the major diameter base of the ring facing outwards). Because of this taper, when the ring 10 is inserted into the hole 52 a better mechanical fit is obtained between the outer surface of the ring 10 and the last inner portion of the hole 52. For simplicity, the taper is shown exaggerated in FIG. 5.

Having chosen from the series of circular rings 10 one which corresponds to the diameter of the cutter used for making the hole 52, and before finally positioning the ring 10 on the step 60, the most suitable columellar element is then chosen from those having intermediate portions 22 of different lengths. The measuring instrument described in Italian patent No. 1,067,273 in the name of the present applicant enables this choice to be made easily and quickly.

The intermediate portion 22 of the columellar element must normally be bent (as shown for example in FIG. 5) to adapt it to the specific patient.

If the stapes is whole and therefore usable, the second connection piece 34 of the columellar element 20 will be of the type shown in FIG. 3. If, however, only the footplate of the stapes is usable, then the second connection piece will be of the type 34' shown in FIG. 4, and will be used as shown in FIG. 5. When the columellar element has been placed in its correct position, it is retained in this position by pieces of reabsorbable fibrin sponge.

To position the ring 10 with its elastic membrane 14, it is necessary only to snap the spherical head 28 of the columellar element 20 through the hole 16 in the membrane 14.

Any spaces between the ring 10 and hole 52 can be filled with the ring material in powdered form.

I claim:

1. A middle ear prosthesis, comprising:
a circular ring having an inner surface and an outer surface, said inner surface defining the ring opening, said circular ring being made of a substance which comprises a substantially rigid synthetic material compatible with the human body and of a type able to bond to the osseous tissue with which it is placed in contact;
an elastic membrane of synthetic material compatible with the human body and fixed to said ring to close said opening, said elastic membrane having an outer edge;
a columellar element of material compatible with the human body and comprising an elongated intermediate portion of substantially rigid but bendable material, said elongated intermediate portion having first and second ends;
a first connection means for releasably connecting said first end of the intermediate portion of the columellar element to a central region of the elastic membrane; and
a second connection means for fixing said second end of said intermediate portion to the stapes of the ear, said second connection means consisting of a piece of substantially rigid synthetic material having means capable of bonding to the osseous tissue with which it comes into contact, wherein said circular ring is placed in the opening of the external acoustic meatus after the opening in the acoustic meatus has been bored to a diameter to fit to the outer surface of said circular ring.

2. A prosthesis as claimed in claim 1, wherein:
said first connection means comprises a spherical head attachable to said intermediate portion; and
a hole is provided in a central region of said elastic membrane, through which said spherical head is insertable.

3. A prosthesis as claimed in claim 1, wherein:
said first connection means comprises a spherical head; and
a hole is formed in a central region of said elastic membrane, and said spherical head is inserted therethrough, thereby engaging said elastic membrane.

4. A prosthesis as claimed in claim 3, wherein said spherical head is formed of the same material as that of said circular ring and said second connection means.

5. A prosthesis as claimed in claim 1, wherein said intermediate portion comprises a biocompatible metal wire.

6. A prosthesis as claimed in claim 5, wherein said metal wire is platinum.

7. A prosthesis as claimed in claim 2, wherein said first connection means further comprises means defining a cavity into which said first end of said intermediate portion of said columellar element is inserted by slight forcing.

8. A prosthesis as claimed in claim 1, wherein:
the inner surface of said circular ring defines an annular cavity sized to receive said outer edge of said elastic membrane; and
said ring comprises means for retaining said edge of said elastic membrane.

9. A prosthesis as claimed in claim 8, wherein said outer surface of said circular ring is tapered to obtain better adherence to the opening in the external acoustic meatus, the opening in the external acoustic meatus being bored to have a taper which corresponds to that of said outer surface of said circular ring.

10. A prosthesis as claimed in claim 1, wherein said second connection means comprises means defining a cavity into which said second end of said intermediate portion can be inserted by slight forcing.

11. A prosthesis as claimed in claim 3, wherein said intermediate portion comprises a biocompatible metal wire.

12. A prosthesis as claimed in claim 4, wherein said intermediate portion comprises a biocompatible metal wire.

13. A prosthesis as claimed in claim 5, wherein said first connection means comprises means defining a cavity into which said first end of said intermediate portion of said columellar element is inserted by slight forcing.

14. A prosthesis as claimed in claim 6, wherein the first connection means comprises means defining a cavity into which said first end of said intermediate portion of said columellar element is inserted by slight forcing.

15. A prosthesis as claimed in claim 3, wherein the inner surface of said circular ring defines an annular cavity sized to receive said outer edge of said elastic membrane, wherein said ring comprises means for retaining said edge of said elastic membrane.

16. A prosthesis as claimed in claim 4, wherein the inner surface of said circular ring defines an annular cavity sized to receive said outer edge of said elastic membrane, wherein said ring comprises means for retaining said edge of said elastic membrane.

17. A prosthesis as claimed in claim 5, wherein the inner surface of said circular ring defines an annular cavity sized to receive said outer edge of said elastic membrane, wherein said ring comprises means for retaining said edge of said elastic membrane.

18. A prosthesis as claimed in claim 6, wherein the inner surface of said circular ring defines an annular cavity sized to receive said outer edge of said elastic membrane, wherein said ring comprises means for retaining said edge of said elastic membrane.

19. A prosthesis as claimed in claim 7, wherein the inner surface of said circular ring defines an annular cavity sized to receive said outer edge of said elastic membrane, wherein said ring comprises means for retaining said edge of said elastic membrane.

20. A series of middle ear prosthesis of varying sizes which cover all possible requirements, each said ear prosthesis comprising:

a circular ring having an inner surface and an outer surface, said inner surface defining the ring opening, said circular ring being made of a substance which comprises a substantially rigid synthetic material compatible with the human body and of a type able to bond to the osseous tissue with which it is place in contact;

an elastic membrane of synthetic material compatible with the human body and fixed to said ring to close said opening, said elastic membrane having an outer edge;

a columellar element of material compatible with the human body and comprising an elongated intermediate portion of substantially rigid but bendable material, said elongated intermediate portion having first and second ends;

a first connection means for releasably connecting said first end of the intermediate portion of the columellar element to a central region of the elastic membrane; and a second connection means for fixing said second end of said intermediate portion to the stapes of the ear, said second connection means consisting of a piece of substantially rigid synthetic material having means capable of bonding to the osseous tissue with which it comes into contact, wherein said circular ring is placed in the opening of the external acoustic meatus after the opening in the acoustic meatus has been bored to a diameter to fit to the outer surface of said circular ring.

* * * * *